United States Patent [19]

Coates et al.

[11] Patent Number: 5,013,733

[45] Date of Patent: May 7, 1991

[54] LACTAM DERIVATIVES

[75] Inventors: Ian H. Coates, Hertford; Alexander W. Oxford; Peter C. North, both of Royston; Thomas Miller, Harefield; Anthony D. Baxter, Iver Heath; Kevin I. Hammond, Ulverston, all of England

[73] Assignee: Glaxo Group Limited, England

[21] Appl. No.: 485,532

[22] Filed: Feb. 27, 1990

[30] Foreign Application Priority Data

Feb. 28, 1989 [GB] United Kingdom ............... 8904551

[51] Int. Cl.⁵ ..................... A61K 31/55; C07D 223/00
[52] U.S. Cl. .................................. 514/213; 514/292; 540/484; 546/86
[58] Field of Search ................ 546/86; 540/484; 514/292, 213

[56] References Cited

FOREIGN PATENT DOCUMENTS

| A-94742 | 11/1983 | European Pat. Off. | 546/112 |
|---|---|---|---|
| A-99789 | 2/1984 | European Pat. Off. | 546/133 |
| A-200444 | 11/1986 | European Pat. Off. | 548/371 |
| 306323 | 3/1989 | European Pat. Off. | 546/86 |
| 339959 | 11/1989 | European Pat. Off. | 546/86 |
| A-350130 | 1/1990 | European Pat. Off. | 546/85 |
| 353983 | 2/1990 | European Pat. Off. | 546/86 |
| 356098 | 2/1990 | European Pat. Off. | 546/86 |
| A-3740352 | 11/1987 | Fed. Rep. of Germany | 546/86 |
| A-2100259 | 6/1981 | United Kingdom | 548/452 |
| A-2125398 | 6/1982 | United Kingdom | 548/469 |

Primary Examiner—Mary C. Lee
Assistant Examiner—Joseph McKane
Attorney, Agent, or Firm—Bacon & Thomas

[57] ABSTRACT

The invention provides lactam derivatives of the general formula (I)

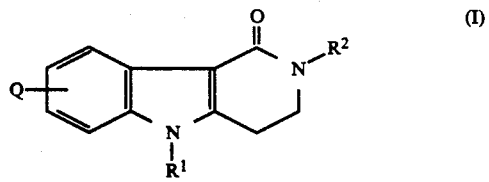

wherein $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, phenylmethoxymethyl, phenoxyethyl, phenoxymethyl, $-CO_2R^3$, $-COR^3$, $-CONR^3R^4$ or $-SO_2R^3$ (wherein $R^3$ and $R^4$, which may be the same or different each represents a hydrogen atom, a $C_{1-6}$alkyl or $C_{3-7}$cycloalkyl group, or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^3$ does not represent a hydrogen atom when $R^1$ represents a group $-CO_2R^3$ or $-SO_2R^3$);

and $R^2$ represents a group of formula (a), (b) or (c):

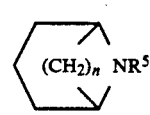

(a)

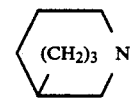

(b)

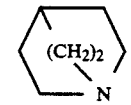

(c)

wherein $R^5$ represents a hydrogen atom or a $C_{1-6}$alkyl, $C_{3-7}$cycloalkyl, $C_{3-6}$alkenyl or phenyl$C_{1-3}$alkyl group;

n represents 2, 3 or 4;

Q represents a hydrogen or a halogen atom, or a hydroxy, $C_{1-4}$alkoxy, phenyl$C_{1-3}$alkoxy or $C_{1-6}$alkyl group or a group $-NH^6R^7$ or $-CONR^6R^7$ wherein $R^6$ and $R^7$, which may be the same or different, each represents a hydrogen atom or a $C_{1-4}$alkyl or $C_{3-4}$alkenyl group, or together with the nitrogen atom to which they are attached form a saturated 5 to 7 membered ring); and physiologically acceptable salts and solvates thereof.

The compounds of formula (I) are potent and selective antagonists of 5-hydroxytryptamine at 5-HT₃ receptors and are useful, for example in the treatment of psychotic disorders, anxiety and nausea and vomiting.

9 Claims, No Drawings

LACTAM DERIVATIVES

This invention relates to lactam derivatives, to processes for their preparation, to pharmaceutical compositions containing them and to their medical use.

In particular the invention relates to compounds which are potent and selective antagonists of 5-hydroxytryptamine (5-HT) at 5-HT receptors of the type located on terminals of primary afferent nerves. Receptors of this type are now designated as 5-HT$_3$ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

The compounds of the present invention posses an azabicyclo moiety. Azabicyclo derivatives having antagonist activity at 5-HT$_3$ receptors have been described previously, for example, in UK Patent Specifications No. 2100259 and 2125398, and European Patent Specification No. 200444. Furthermore, European Patent Specification Nos. 94742 and 99789 also describe azabicyclo derivatives which have since been demonstrated to possess 5-HT$_3$ antagonist activity. The compounds of the present invention differ in structure from azabicyclo derivatives that have been described previously.

Thus, the present invention provides a novel tricyclic lactam of the general formula (I):

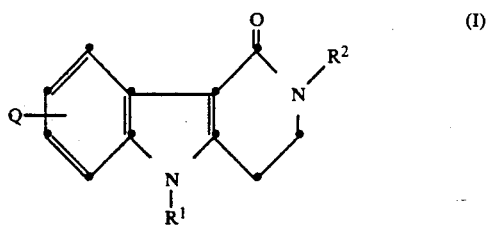

(I)

wherein $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkylC$_{1-4}$alkyl, phenyl, phenylC$_{1-3}$alkyl, phenylmethoxymethyl, phenoxyethyl, phenoxymethyl, —CO$_2$R$^3$, —COR$^3$, —CONR$^3$R$^4$ or —SO$_2$R$^3$ (wherein R$^3$ and R$^4$, which may be the same or different, each represents a hydrogen atom, a C$_{1-6}$alkyl or C$_{3-7}$cycloalkyl group, or a phenyl or phenylC$_{1-4}$alkyl group, in which the phenyl group is optionally substituted by one or more C$_{1-4}$alkyl, C$_{1-4}$alkoxy or hydroxy groups or halogen atoms, with the proviso that R$^3$ does not represent a hydrogen atom when R$^1$ represents a group —CO$_2$R$^3$ or —SO$_2$R$^3$); and R$^2$ represents a group of formula (a), (b) or (c):

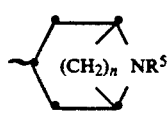

(a)

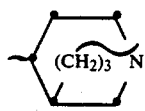

(b)

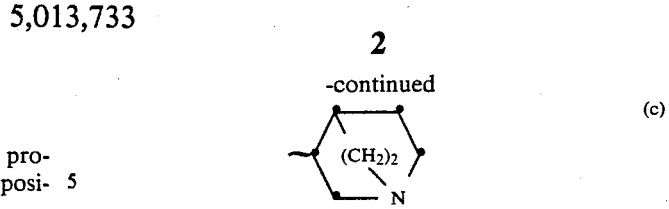

(c)

wherein R$^5$ represents a hydrogen atom or a C$_{1-6}$alkyl, C$_{3-7}$cycloalkyl, C$_{3-6}$alkenyl or phenylC$_{1-3}$alkyl group;

n represents 2, 3 or 4;

Q represents a hydrogen or a halogen atom, or a hydroxy, C$_{1-4}$alkoxy, phenylC$_{1-3}$alkoxy or C$_{1-6}$alkyl group or a group —NR$^6$R$^7$ or —CONR$^6$R$^7$ wherein R$^6$ and R$^7$, which may be the same or different, each represents a hydrogen atom or a C$_{1-4}$alkyl or C$_{3-4}$alkenyl group, or together with the nitrogen atom to which they are attached form a saturated 5 to 7 membered ring); and physiologically acceptable salts and solvates thereof.

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvates may, for example, be hydrates.

All optical isomers of compounds of general formula (I) and their mixtures including the racemic mixtures thereof, and all the geometric isomers of compounds of formula (I), are embraced by the invention.

Referring to the general formula (I), an alkyl group may be a straight chain or branched chain alkyl group, for example, methyl, ethyl, n-propyl, prop-2-yl, n-butyl, but-2-yl, 2-methylprop-2-yl, n-pentyl, pent-3-yl or n-hexyl. A C$_{3-6}$alkenyl group may be, for example, a propenyl or butenyl group. When R$^1$ represents a C$_{3-6}$alkenyl or C$_{3-10}$alkynyl group, or R$^5$ represents a C$_{3-6}$alkenyl group, the double or triple bond may not be adjacent to the nitrogen atom. A phenylC$_{1-3}$alkyl group may be, for example, a benzyl, phenethyl or 3-phenylpropyl group. A C$_{3-7}$cycloalkyl group may be, for example, a cyclopropyl, cyclobutyl, cyclopentyl, cyclohexyl or cycloheptyl group. When Q represents a C$_{1-4}$alkoxy group it may be, for example, a methoxy group. When 0 represents a halogen atom it may be, for example, a fluorine, chlorine or bromine atom. The substituent Q may be at the a, b, c or d position of the indole moiety:

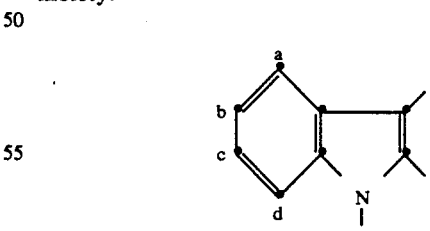

According to one aspect, the invention provides compounds of formula (I) wherein Q represents a hydrogen atom, and R$^1$ and R$^2$ are as defined above in formula (I).

A preferred class of compounds of formula (I) is that wherein R$^1$ represents a hydrogen atom or a C$_{1-4}$alkyl, C$_{3-4}$alkenyl, C$_{3-4}$alkynyl, C$_{5-6}$cycloalkyl, C$_{5-6}$cycloalkylmethyl, phenylC$_{1-2}$alkyl, phenylmethoxymethyl or N,N-diC$_{1-3}$alkylcarboxamido group.

A particularly preferred group of compounds of formula (I) is that wherein $R^1$ represents a $C_{1-4}$alkyl (e.g. methyl group).

Another preferred class of compounds of formula (I) is that wherein $R^2$ represents a group of formula (a) or (c). When $R^2$ represents a group of formula (a), n is preferably 2 and $R^5$ is preferably a $C_{1-3}$alkyl (e.g. methyl) group.

A particularly preferred class of compounds of formula (I) is that wherein $R^2$ represents a group of formula (c).

Another preferred class of compound of formula (I) is that wherein Q represents a hydrogen atom.

A particularly preferred compound according to the invention is 2-(1-azabicyclo[2.2.2]oct-3-yl)-2,3,4,5-tetrahydro-5-methyl-1H-pyrido-[4,3-b]indol-1-one and its physiologically acceptable salts and solvates.

The potent and selective antagonism of 5-HT at 5-HT₃ receptors by compounds of the invention has been demonstrated by their ability to inhibit 3-(5-methyl-1H-imidazol-4-yl)-1-[1-(methyl-t₃)-1H-indol-3-yl]-1-propanone binding in rat entorhinal cortex homogenates (following the general procedure described by G. Kilpatrick et al. in *Nature*, 1987, 330, 746), and/or by their ability to inhibit the 5-HT-induced depolarisation of the rat isolated vagus nerve preparation.

Compounds of formula (I), which antagonise the effect of 5-HT at 5-HT₃ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome; migraine; pain; dependency on drugs or substances of abuse; depression; or dementia or another cognitive disorder which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine, cimetidine, famotidine, nizatidine or roxatidine) or $H^+K^+ATPase$ inhibitors (e.g. omeprazole). In the treatment of nausea and vomiting, compounds of formula (I) may also be administered in combination with dexamethasone or a cyclo-oxygenase inhibitor such as piroxicam.

A proposed dose of the compounds of the invention for administration to man (of approximately 70 kg body weight) is 0.001 to 100 mg, preferably 0.01 to 50 mg, more preferably 0.1 to 20 mg of the active ingredient per unit dose expressed as the weight of free base, which could be administered, for example, 1 to 4 times per day. It will be appreciated that it may be necessary to make routine variations to the dosage, depending on the age and condition of the patient. The dosage will also depend on the route of administration.

Compounds of general formula (I) and physiologically acceptable salts or solvates thereof may be prepared by the general methods outlined hereinafter. In the following description, the groups Q, $R^1$ and $R^2$ are as defined for compounds of general formula (I) unless otherwise stated.

According to a first general process (A), a compound of general formula (I) may be prepared by reacting a compound of formula (II):

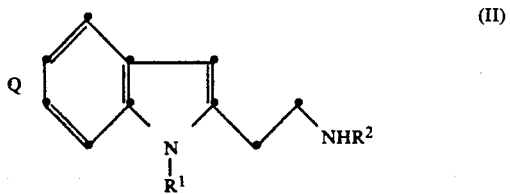

(II)

or a protected derivative thereof, with phosgene in the presence of a Lewis acid; or with carbon monoxide in the presence of a palladium (II) salt, followed where necessary by removal of any protecting groups.

When the reaction is effected with phosgene, the Lewis acid may be, for example, anhydrous aluminium trichloride or stannic chloride, and the reaction may conveniently be effected in an inert solvent such as an aromatic hydrocarbon (e.g. toluene) or a halogenated hydrocarbon (e.g. dichloromethane), or mixtures thereof, at a temperature between ambient and 100° C. and at atmospheric pressure.

When the reaction is effected with carbon monoxide, the palladium (II) salt may be, for example, palladium acetate or palladium chloride, and triphenylphosphine and a base such as triethylamine are preferably present. The reaction may conveniently be carried out in a solvent such as acetonitrile at the reflux temperature of the solvent, and at atmospheric pressure.

According to another general process (B), a compound of general formula (I) may be converted into another compound of formula (I) using conventional techniques. Such conventional techniques include hydrogenation, alkylation and acylation using protection and deprotection where necessary.

Thus, according to one embodiment of the interconversion process (B), hydrogenation may be used to convert an alkenyl or an alkynyl substituent into an alkyl substituent, or an alkynyl into an alkenyl substituent. Hydrogenation may also be used to replace a phenylmethoxymethyl group by a hydrogen atom. Hydrogenation according to general process (B) may be effected using conventional procedures, for example, using hydrogen in the presence of a catalyst, as described in European Patent Specification No. 242973.

The term 'alkylation' according to general process (B) includes the introduction of groups such as cycloalkyl, alkenyl or phenalkyl groups.

Thus, for example, a compound of formula (I) in which $R^1$ represents a $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl$C_{1-3}$alkyl, phenylmethoxymethyl, phenoxyethyl or phenoxymethyl group may be prepared by alkylating a compound of formula (I) in which $R^1$ represents a hydrogen atom, or a compound in which $R^5$ represents a $C_{1-6}$alkyl, $C_{3-7}$cycloalkyl, $C_{3-6}$alkenyl or phenyl$C_{1-3}$alkyl group may be prepared by alkylating the corresponding compound of formula (I) in which $R^5$ represents a hydrogen atom, or a compound in which Q represents a $C_{1-4}$alkoxy or phenyl$C_{1-3}$alkoxy group may be prepared by alkylating the corresponding compound of formula (I) in which Q represents a hydroxyl group, using conventional procedures, for example as described in published European Patent Specification No. 242973. Thus the reactions may be effected using an appropriate alkylating agent of formula $R^8Z$ (where $R^8$ is the group to be introduced and Z is a leaving atom or group), preferably in the presence of a base.

According to another embodiment of general process (B), a compound of formula (I) wherein $R^1$ represents $-CO_2R^3$, $-COR^3$, $-CONR^3R^4$ or $-SO_2R^3$ may be prepared by acylating or sulphonylating as appropriate, a compound of formula (I) wherein $R^1$ represents a hydrogen atom. The acylation/sulphonylation reactions may be effected using an appropriate acylating-/sulphonylating agent according to conventional procedures, for example, as described in published European Patent Specification No. 210840.

It should be appreciated that in the above transformations it may be necessary or desirable to protect any sensitive groups in the molecule of the compound in question to avoid undesirable side reactions. For example, it may be necessary to protect the indole nitrogen atom and/or the nitrogen atom in the group of formula (a), for example with an arylmethyl (e.g. trityl), arylmethoxymethyl (e.g. phenylmethoxymethyl), alkyl (e.g. t-butyl), alkoxymethyl (e.g. methoxymethyl), acyl (e.g. benzylcarbonyl) or a sulphonyl (e.g. N,N-dimethylaminosulphonyl or p-toluenesulphonyl) group.

Thus according to another general process (C), a compound of general formula (I) may be prepared by the removal of any protecting groups from a protected form of a compound of formula (I). Deprotection may be effected using conventional techniques such as those described in 'Protective Groups in Organic Synthesis' by T. W. Greene (John Wiley and Sons. 1981).

For example, an arylmethoxymethyl N-protecting group may be cleaved by hydrogenolysis in the presence of a catalyst (e.g. palladium on charcoal). A trityl group may be cleaved by acid hydrolysis (e.g. using dilute hydrochloric or acetic acid). An alkoxyalkyl group may be removed using a mineral acid (e.g. dilute hydrochloric or hydrobromic acid). An acyl group may be removed by hydrolysis under acidic or basic conditions (e.g. using hydrogen bromide, dilute hydrochloric acid or sodium hydroxide). A sulphonyl group may also be removed by alkaline or acidic hydrolysis.

Compounds of formula (II) may be prepared, for example, by reacting a compound of formula (III):

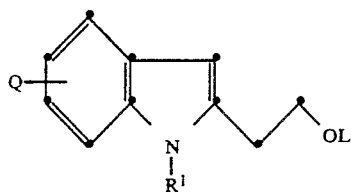

(III)

wherein L represents a leaving atom or group, such as a sulphonyloxy (e.g. p-toluenesulphonyloxy or methanesulphonyloxy) group or a halogen (e.g. chlorine, bromine or iodine) atom; or a protected derivative thereof, with a compound of formula (IV):

$R^2NH_2$ (IV)

or a protected derivative thereof in the presence of an acid acceptor such as diisopropylethylamine, at an elevated temperature.

Compounds of formula (III) may be prepared from a compound of formula (V):

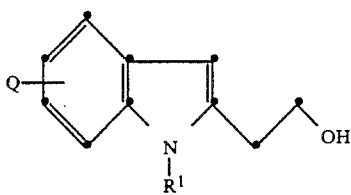

(V)

or a protected derivative thereof using conventional procedures. Thus, for example, a compound of formula (III) in which L represents a sulphonyloxy group may be prepared by reacting a compound of formula (V) with a sulphonylating agent (e.g. tosyl chloride or methanesulphonyl chloride), and a compound of formula (III) in which L represents a halogen atom may be prepared by reacting a compound of formula (V) with a halogenating reagent (e.g. thionyl chloride).

Compounds of formulae (IV) and (V) are either known, or may be prepared from known compounds by conventional procedures.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), a halogenated hydrocarbon (e.g. dichloromethane), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers (e.g a racemic mixture) using conventional means, such as an optically active resolving acid; see for example 'Stereochemistry of Carbon Compounds' by E. L. Eliel (McGraw Hill, 1962) and 'Tables of Resolving Agents' by S. H. Wilen.

The methods described above for preparing the compounds of the invention may be used for the introduction of the desired groups at any stage in the stepwise formation of the required compounds, and it will be appreciated that these methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples. All temperatures are in °C. Thin layer chromatography (t.l.c.) was carried out on silica, and flash column chromatography (FCC) on silica (Merck 9385). Solvent System A as used for chromatography denotes dichloromethane:ethanol:0.88 ammonia solution. Organic extracts were dried, where indicated, over magnesium sulphate or sodium sulphate. The following abbreviation is used: THF—tetrahydrofuran.

INTERMEDIATE 1

1-Methyl-1H-indole-2-acetic acid

A mixture of ethyl 1-methyl-1H-indole-2-acetate (5.0 g) and 2N sodium hydroxide (50 ml) was heated to reflux for 4 h. After cooling, the reaction mixture was extracted with ethyl acetate (2x50 ml) and theresulting aqueous solution was made acidic (pH 1) by addition of 2N hydrochloric acid. The resulting solid was filtered off, washed with ether (100 ml) and dried in vacuo to give the title compound (2.1 g), m.p. 146-148°.

INTERMEDIATE 2

Endo-1-methyl-N-(9-methyl-9-azabicyclo[3.3.1]non-3-yl)-1H-indole-2-acetamide maleate A suspension of 1-methyl-1H-indole-2-acetic acid (189 mg) in dry THF (20 ml) was treated with 1,1'-carbonyldiimidazole (170 mg) at 0° and the mixture was stIrred under nitrogen for 30 min. A solution of endo-9-methyl-9-azabicyclo[3.3.1]non-3-yl amine (154 mg) in dry THF (2 ml) was then added, and the reaction mixture was allowed to warm to room temperature over 1 h. The reaction mixture was then poured into 5N sodium hydroxide (50 ml) and the organic layer was separated and extracted with ether (50 ml). The organic extract was washed with water (50 ml), dried and concentrated onto silica. FCC eluting with System A (100:8:1) gave a solid (108 mg), a portion of which (95 mg) was dissolved in dry methanol. Maleic acid (35 mg) was added and the solution was heated on a steam bath for 10 min. After cooling, dry ether was added to precipitate a solid which was filtered off to give the title compound (82 mg), m.p. 201-203°.

INTERMEDIATE 3

Endo-1-methyl-(9-methyl-9-azabicyclo[3.3.1]non-3-yl)-1H-indole-2-ethanamine

A solution of endo-1-methyl-N-(9-methyl-9-azabicyclo[3.3.1]non-3-yl)-1H-indole-2-acetamide (2.38 g) in dry THF (70 ml) was treated portionwise with lithium aluminium hydride (400 mg) over 15 min under nitrogen with stirring. When addition was complete, stirring was continued for 3 h at room temperature. The mixture was then heated to reflux, and after 30 min further lithium aluminium hydride (250 mg) was added and reflux was continued overnight. After cooling, water (10 ml) was cautiously added followed by sodium sulphate and the mixture was filtered through Hyflo. The filter cake was washed with ether, and the combined organic filtrates were concentrated onto silica. FCC eluting with System A (75:8:1) gave the title compound (100 mg) as an oil, t.l.c. (System A, 75:8:1) Rf 0.15.

INTERMEDIATE 4

N-(1-Azabicyclo[2.2.2]oct-3-yl)-1-methyl-1H-indole-2-acetamide

To a solution of 1-methyl-1H-indole-2-acetic acid (830 mg) in THF (20 ml) was added 1,1'-carbonyldiimidazole (782 mg), and the mixture was stirred for 1 h. 3-Aminoquinuclidine dihydrochloride (960 mg) was then added, followed by triethylamine (2.34 g), and the mixture was stirred overnight at room temperature. The mixture was then poured into brine (200 ml) and extracted with ethyl acetate (2x200 ml). The combined, dried organic extracts were evaporated in vacuo to give a solid which was purified by FCC eluting with System A (50:8:1) to give the title compound (1.30 g), m.p. 185–187°.

INTERMEDIATE 5

N-(1-Azabicyclo[2.2.2]oct-3-yl)-1-methyl-1H-indole-2-ethanamine

To a solution of N-(1-azabicyclo[2.2.2]oct-3-yl)-1-methyl-1H-indole 2-acetamide (1.4 g) in dry THF (30 ml) under nitrogen was added borane (1M solution in THF; 30 ml), and the mixture was heated under reflux for 3 h and then cooled in ice. Methanol (10 ml) was added dropwise followed by 5M hydrochloric acid (50 ml), and the mixture was then heated at reflux for 4 h. The cooled solution was poured into 2M sodium hydroxide solution (200 ml), and the mixture was extracted with ethyl acetate (2x200 ml). The combined, dried organic extracts were evaporated in vacuo to give an oil which was dissolved in dry THF (45 ml). 2,3-Dichloro-5,6-dicyano-1,4-benzoquinone (1.13 g) was added slowly in small portions over 15–20 min and the resulting suspension was stirred for 30 min. The mixture was diluted with ethyl acetate (250 ml) and washed with 2M sodium hydroxide solution (2x250 ml). The organic layer was dried and evaporated in vacuo to give a gum which was purified by FCC eluting with System A (75:8:1) to give the title compound (354 mg) as an oil, t.l.c. (System A,75:8:1) Rf 0.24.

INTERMEDIATE 6

Endo-1-methyl-N-[8-methyl-8-azabicyclo[3.2.1]oct-3-yl]-1H-indole-2-ethanamine

To a solution of 2-(2-hydroxyethyl)-1-methyl indole (1.5 g) in dichloromethane (25 ml) was added pyridine (1.5 ml), followed by tosyl chloride (1.96 g), and the reslutng solution was stirred at room temperature for 24 h. The solvent was removed in vacuo and the residue was purified by FCC eluting with ether:hexane (3:2) to give a solid (2.80 g) which was dissolved in acetonitrile (20 ml). Diisopropylethylamine (2 ml) was added, followed by tropinamine (1.2 g) in acetonitrile (5 ml), and the resulting solution was heated at reflux for 24 h. The solution was then poured into dichloromethane (200 ml), washed with 2M sodium hydroxide solution (200 ml), dried and the solvent was removed in vacuo to leave an oil which was purified by FCC eluting with System A (75:8:1) to give the title compound (0.7 g) as a solid, m.p. 92–93.5°.

EXAMPLE 1

Endo-2,3,4,5-tetrahydro-5-methyl-2-(9-methyl-9-azabicyclo[3.3.1]non-3-yl)-1H-pyrido [4,3-b]indol-1-one maleate A solution of endo-1-methyl-(9-methyl-9-azabicyclo[3.3.1]non-3-yl)-1H-indole-2-ethanamine (160 mg) in dry dichloromethane (5 ml) was added dropwise to a stirred solution of phosgene in toluene (12.5% w/v; 1 ml) in dry dichloromethane (5 ml) at 0° under nitrogen. The resulting solution was stirred at 0° for a further 2.5 h, and then concentrated in vacuo (keeping temperature <40°) to give a solid. This was redissolved in dry dichloromethane (10 ml), aluminium trichloride (80 mg) was added, and stirring was continued under nitrogen for a further 18 h. The reaction mixture was then poured into 5N sodium hydroxide (50 ml) and extracted with dichloromethane (2x50 ml). The combined, dried organic extracts were concentrated onto silica (Merck 9385), and FCC eluting with System A (75:8:1) gave a solid (42 mg). This solid was dissolved in methanol (5 ml), maleic acid (15 mg) was added, and the mixture was heated on a steam bath for 10 min. After cooling, dry ether was added dropwise to precipitate a solid which was filtered off to give the title compound (51 mg), m.p. 216–218°, t.l.c. (System A, 75:8:1)RF 0.33.

EXAMPLE 2

2-(1-Azabicyclo[2.2.2]oct-3-yl)-2,3,4,5-tetrahydro-5-methyl-1H-pyrido[4,3-b]indol-1-one maleate A solution of phosgene in toluene (12.5% w/v; 5 ml) in dry dichloromethane (5 ml) was cooled to 0° under nitrogen. N-(1-Azabicyclo[2.2.2]oct-3-yl)-1-methyl-1H-indol-2-ethanamine (350 mg) in dichloromethane (5 ml) was added slowly, and the mixture was stirred for 2 h. The solvent was removed in vacuo and the residue was redissolved in dichloromethane (10 ml). Aluminium trichloride (181 mg) was added, and the mixture was stirred overnight at room temperature. The mixture was then poured into 2M sodium hydroxide solution (100 ml) and extracted with ethyl acetate (2x100 ml). The combined, dried organic extracts were evaporated in vacuo to give a gum which was purified by FCC eluting with System A (100:8:1) to give a solid (27 mg). 1his was dissolved in ethanol (5 ml), and maleic acid (10 mg) in ethanol (5 ml) was added. The solvent was removed in vacuo, and the residue was triturated with ethyl acetate and filtered off to give the title compound (31 mg), m.p. 194–196°, t.l.c. (System A, 100:8:1) Rf 0.16.

EXAMPLE 3

Endo-2,3,4,5-tetrahydro-5-methyl-2-[8-methyl-8-azabicyclo[3.2.1]oct-3-yl]-1H-pyrido[4,3-b]indol-1-one Endo-1-methyl-N-[8-methyl-8-azabicyclo[3.2.1]oct-3-yl]-1H-indole-2-ethanamine (1.016 g), palladium acetate (760 mg) triphenylphosphine (17.8 g) and triethylamine (6 ml) were suspended in dry acetonitrile (30 ml). The mixture was then stirred at reflux under an atmosphere of carbon monoxide for 18 h. The cooled mixture was filtered through Hyflo and the filter pad was washed with ethyl acetate (100 ml). The combined filtrates were evaporated in vacuo to leave a gum which was purified by FCC eluting with System A (100:8:1) to give a solid. Crystallisation of this solid from ethyl acetate gave the title compound (221 mg), m.p. 206–207°.

Analysis: Found: C,74.2; H,8.0; N,12.85; $C_{20}H_{25}N_3O$ requires C,74.3; H,7.8; N,13.0%.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Tablets of other strengths may be prepared by altering the ratio of active ingredient to excipients or the compression weight and using punches to suit.

Direct Compression Tablet

| Direct Compression Tablet | mg/tablet |
| --- | --- |
| Active Ingredient | 0.50 |
| Calcium Hydrogen Phosphate BP* | 87.25 |
| Croscarmellose Sodium NF | 1.80 |
| Magnesium Stearate BP | 0.45 |
| Compression weight | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

INJECTION FOR INTRAVENOUS ADMINISTRATION

|  | mg/ml | |
| --- | --- | --- |
| Active ingredient | 0.05 | 1.0 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

We claim:

1. A compound of formula (I)

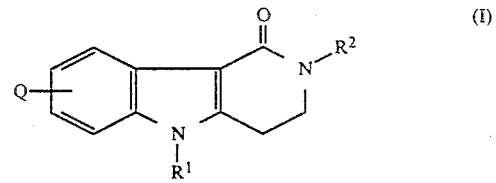

wherein $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, phenylmethoxymethyl, phenoxyethyl, phenoxymethyl, $-CO_2R^3$, $-COR^3$, $-CONR^3R^4$ or $-SO_2R^3$ (wherein $R^3$ and $R^4$, which may be the same or different each represents a hydrogen atom, a $C_{1-6}$alkyl or $C_{3-7}$cycloalkyl group, or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^3$ does not represent a hydrogen atom when $R^1$ represents a group $-CO_2R^3$ or $-SO_2R^3$);

and $R^2$ represents a group of formula (a), (b) or (c):

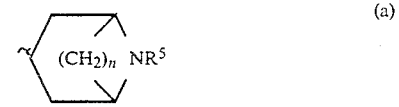

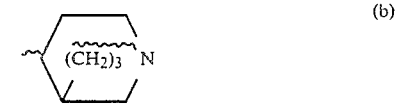

wherein $R^5$ represents a hydrogen atom or a $C_{1-6}$alkyl, $C_{3-7}$cycloalkyl, $C_{3-6}$alkenyl or phenyl$C_{1-3}$alkyl group;

n represents 2, 3 or 4;

Q represents a hydrogen or a halogen atom, or a hydroxy, $C_{1-4}$alkoxy, phenyl$C_{1-3}$alkoxy or $C_{1-6}$alkyl group or a group $-NR^6R^7$ or $-CONR^6R^7$ wherein $R^6$ and $R^7$, which may be the same or different, each represents a hydrogen atom or a $C_{1-4}$alkyl or $C_{3-4}$alkenyl group, or together with the nitrogen atom to which they are attached form a saturated 5 to 7 membered ring);

or a physiologically acceptable salt or solvate thereof.

2. A compound according to claim 1 in which $R^1$ represents a hydrogen atom or a $C_{1-4}$alkyl, $C_{3-4}$alkenyl, $C_{3-4}$alkynyl, $C_{5-6}$cycloalkyl, $C_{5-6}$cycloalkylmethyl, phenyl$C_{1-2}$alkyl, phenylmethoxymethyl or N,N-di$C_{1-3}$alkylcarboxamido group.

3. A compound according to claim 1 in which $R^1$ represents a $C_{1-4}$alkyl group.

4. A compound according to claim 1 in which $R^2$ represents a group of formula (a), n is 2 and $R^5$ is a $C_{1-3}$alkyl group.

5. A compound according to claim 1 in which $R^2$ represents a group of formula (c).

6. A compound according to claim 1 in which Q represents a hydrogen atom.

7. 2-(1-Azabicyclo[2.2.2]oct-3-yl)-2,3,4,5-tetrahydro-5-methyl-1H-pyrido[4,3-b]indol-1-one or a physiologically acceptable salt or solvate thereof.

8. A pharmaceutical composition which comprises an effective amount of a compound of formula (I) as defined in claim 1 or a physiologically acceptable salt or solvate thereof together with at least one physiologically acceptable carrier or excipient.

9. A method of treating a condition mediated through 5-$HT_3$ receptors which comprises administering to a patient an effective amount to relieve said condition of a compound of formula (I) as defined in claim 1 or a physiologically acceptable salt or solvate thereof.

* * * * *